United States Patent [19]

Watanabe

[11] 4,045,672
[45] Aug. 30, 1977

[54] APPARATUS FOR TOMOGRAPHY COMPRISING A PIN HOLE FOR FORMING A MICROBEAM OF X-RAYS

[75] Inventor: Eiji Watanabe, Akishima, Japan

[73] Assignee: Nihon Denshi Kabushiki Kaisha, Tokyo, Japan

[21] Appl. No.: 720,409

[22] Filed: Sept. 3, 1976

[30] Foreign Application Priority Data

| Sept. 11, 1975 | Japan | 50-110230 |
| Sept. 11, 1975 | Japan | 50-110231 |
| Dec. 19, 1975 | Japan | 50-152074 |
| Feb. 5, 1976 | Japan | 51-11591 |
| Feb. 28, 1976 | Japan | 51-21711 |
| Mar. 5, 1976 | Japan | 51-23997 |

[51] Int. Cl.$^2$ ............ A61B 6/02; G01N 23/08; G03B 41/16; H05G 1/30
[52] U.S. Cl. ............................ 250/360; 250/445 T
[58] Field of Search ........... 250/360, 366, 369, 445 T, 250/416 TV, 403

[56] References Cited

U.S. PATENT DOCUMENTS

| 4,002,917 | 1/1977 | Mayo | 250/445 T |
| 4,010,370 | 3/1977 | Lemay | 250/445 T |

*Primary Examiner*—Alfred E. Smith
*Assistant Examiner*—T. N. Grigsby
*Attorney, Agent, or Firm*—Webb, Burden, Robinson & Webb

[57] ABSTRACT

In an X-ray generating column, an X-ray microbeam is generated by irradiating a target with a scanning finely focused electron beam and permitting the microbeam to pass a pin hole in a beam guide plate or baffle. The take off direction of the X-ray microbeam is varied by scanning said electron beam over the target. The X-ray microbeam irradiates and passes through a thin slice plane of an object. The X-ray generating column rotates around the object. The rotation and electron beam scanning signals and the output signal of a detector for the X-rays passed through object are memorized by a memory circuit. A calculating circuit then calculates the X-ray absorption coefficient at each micro matrix area on the slice plane of the object, and delivers the respective outputs to an image display means to display an X-ray image of a slice plane of the object.

14 Claims, 13 Drawing Figures

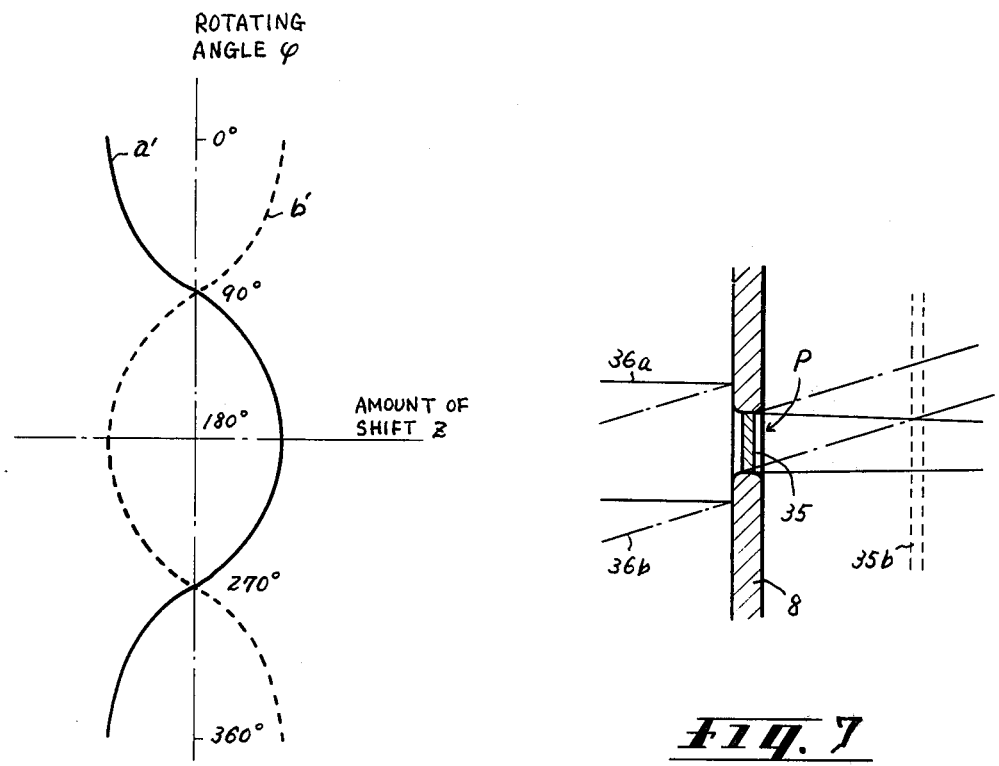
Fig. 6
Fig. 7
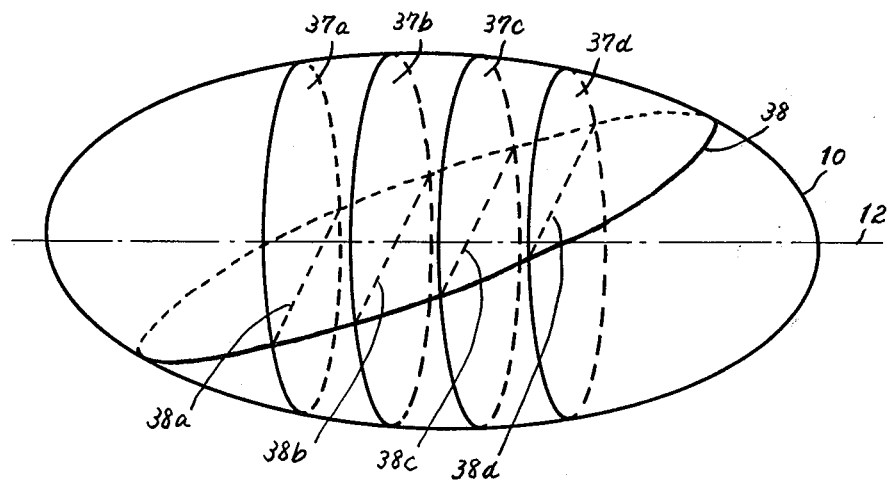
Fig. 8

APPARATUS FOR TOMOGRAPHY COMPRISING A PIN HOLE FOR FORMING A MICROBEAM OF X-RAYS

This invention relates to an apparatus for observing the three-dimensional structure of an object by means of x-ray irradiation.

A method of examining an object by X-ray radiation known as computered tomography was recently developed with a view to obtaining more detailed information than hitherto possible with the conventional X-ray projection image. In this method, the X-ray source is orbited about an axis of an object and X-rays from the source irradiate and pass through a slice plane of the object. At the same time, the X-rays transmitted through the slice plane are detected at each irradiation path. By so doing, each matrix area on the slice plane is irradiated many times by an X-ray beam in many different directions and the X-ray absorption coefficient at each matrix area is calculated by the computer from the results of said transmitted X-ray detection and the position data of the irradiating X-ray path. The X-ray image of the slice plane is then obtained by displaying the X-ray absorption coefficients of the respective matrix areas two-dimensionally.

This method, however, has certain disadvantages in that the apparatus embodying said method is very complicated and cumbersome; moreover, in order to obtain information on one X-ray image in one slice plane, a relatively long measuring time is required.

Accordingly, the main object of this invention is to reduce the measuring time for obtaining one X-ray image of one slice plane of an object.

Yet another object of this invention is to simplify the mechanical measuring apparatus for carrying out computer tomography.

These objects are achieved by using an X-ray generating apparatus incorporating a scanning deflecting device for scanning the electron beam over the surface of a target so as to change the direction of the X-ray microbeam irradiating the object.

Other features and advantages of this invention will become apparent from the following description read with the accompanying drawings of which:

FIG. 6 is a drawing for explaining the embodiment shown in FIG. 5;

FIG. 7 shows, in detail, the beam guide plate of the embodiment shown in FIGS. 1 and 5;

FIG. 8 is a drawing for explaining the signal processing procedure according to this invention;

Figure 1:
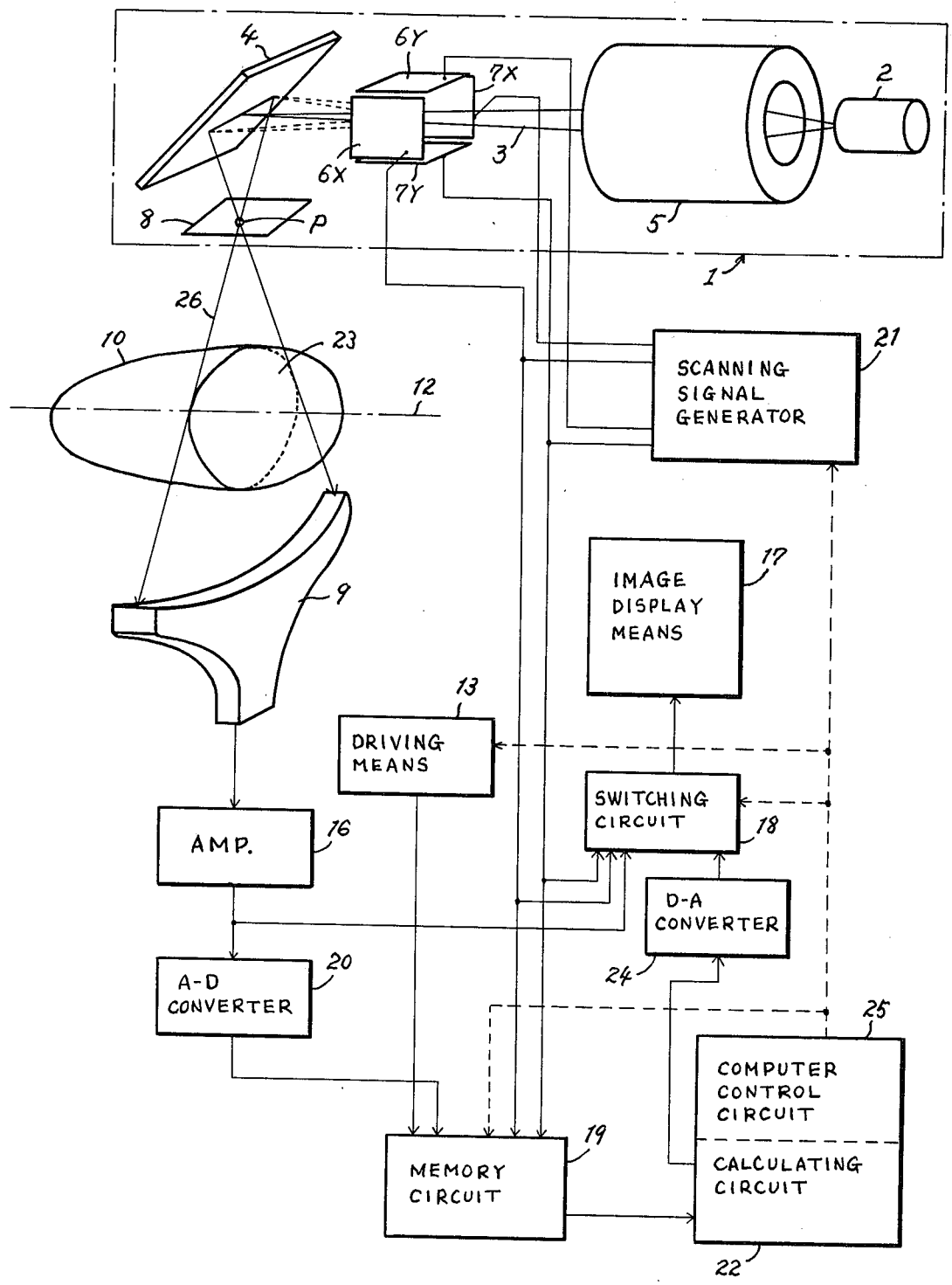
FIG. 1 is a schematic drawing showing one embodiment of this invention.

Referring to FIG. 1, the vacuum column of an X-ray generating apparatus is represented by the dashed line enclosure 1, said column containing an electron beam source 2 for generating an electron beam 3, a target 4, a condenser lens 5 for focusing the electron beam 3 on said target 4, deflecting means 6X, 7X, 6Y and 7Y, and a beam guide plate 8 having a pin hole P. An X-ray detector 9 consists essentially of a large scintillator, a photomultiplier and a collimator for preventing the detection of scattered X-rays, said X-ray detector being arranged opposite the beam guide plate 8 of the vacuum column 1. An object or body 10 is located between the beam guide plate 8 and the X-ray detector 9.

Figure 2:
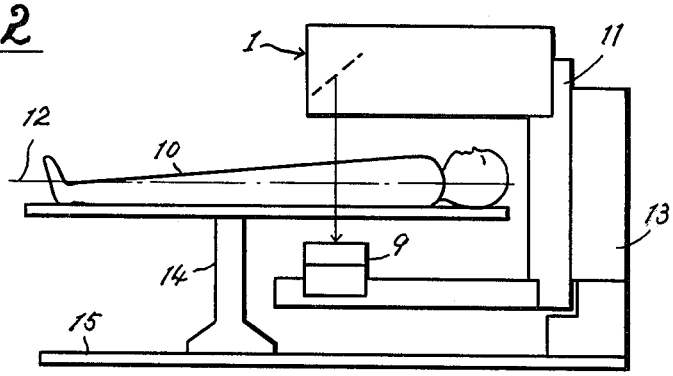
FIGS. 2, 3 and 4 are drawings for explaining the embodiment shown in FIG. 1.

Returning to FIG. 2, a rotatable supporting member 17 supports the vacuum column 1 and the X-ray detector 9, said supporting member 11 serving to rotate the column 1 and the detector 9 around an axis 12 passing through the object 10 reclining on a table 14. Driving means 13, supported on a base 15, is interlocked with said rotatable supporting member 11 to cause rotation of the column 1 and the detector 9.

Referring again to FIG. 1, the output of amplifier 16 is applied to an image display means 17 via a switching circuit 18. The output of said amplifier is also applied to a memory circuit 19 via an A-D converter 20. The outputs of a scanning signal generator 21 are applied to the deflecting means 6X, 7X, 6Y and 7Y, the memory circuit 19 and the image display means 17 via switching circuit 18. A calculating circuit 22 calculates the X-ray absorption coefficient of each matrix area on the cross-sectional slice plane 23 of the object 10 from signals read out of the memory circuit 19. The output of the calculating circuit 22 is applied to the image display means 17 via a D-A converter 24 and the switching circuit 18. A computer control circuit 25 controls the calculating circuit 22, memory circuit 19, driving means 13, switching circuit 18, and scanning signal generator 21 (short dashed lines on FIG. 1).

Figure 3:
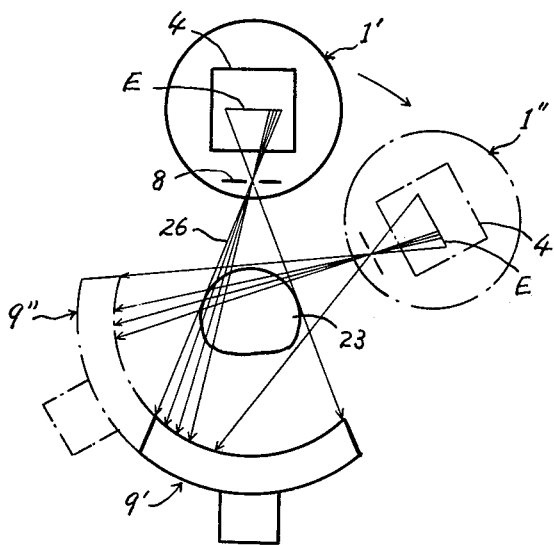

When the computer control circuit 25 applies signals to the various other circuits to obtain a tomograph X-ray image of the slice plane 23 of the object 10, the scanning signal generator 21 applies signals to deflecting means 6X, 7X, 6Y and 7Y so as to sweep the electron beam over the target 4 in a direction E perpendicular to the line connecting pin hole P and axis 12, as shown in FIG. 3, which shows a sectional view of the embodiment of FIG. 1. Consequently, the X-ray microbeam 26 passed through pin hole P irradiates and scans the entire slice plane 23. The computer control circuit 25 controls the driving means 13 to move the vacuum column 1 digitally in an orbit around the axis 12, for example, in FIG. 3 from 1' and 9' to 1" and 9" after completing an X-ray microbeam scan at each stop. In this way, the driving means 13 rotates the vacuum column 1 and the detector 9 several degrees at a time around the axis 12 over a range of more than 100°. During the above rotary sequence, the output signals from the X-ray detector 9 are fed into the memory circuit 19 via the amplifier 16 and the A-D converter 20 together with the output signals from the scanning signal generator 21 and those from the driving means 13. These memorized signals are read-out to the calculating circuit 22 and used for calculating the X-ray absorption coefficient of individual matrix areas on the slice plane 23. The calcualted signals are then fed into the image display means 17 via the D-A converter 24 and switching circuit 18 so that an X-ray image of the slice plane 23 of the object body 10 is displayed thereon.

Figure 4:
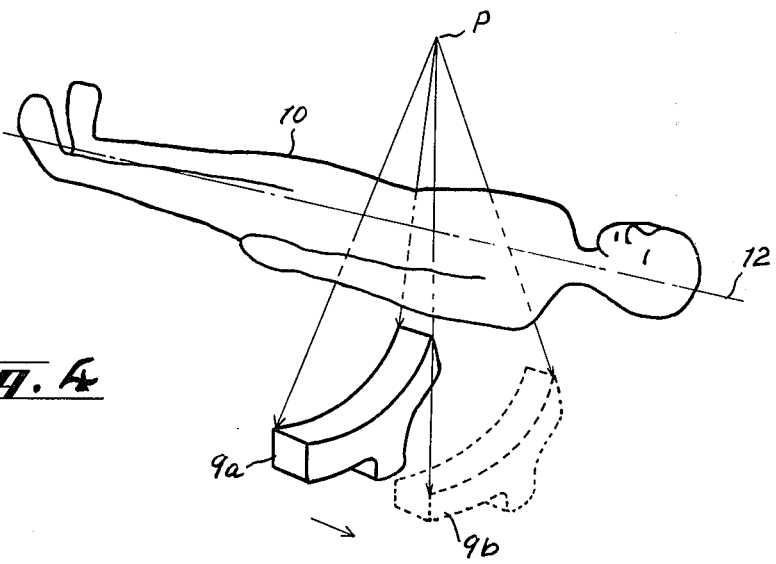

Next, when the computer control circuit 25 applies control signals to the various circuits in order to obtain an X-ray projection image, the vacuum column 1 and X-ray detector 9 remain stationary at a certain position and the scanning signal generator 21 generates a scanning signal which scans the electron beam 3 over the target 4 two-dimensionally. Consequently, the X-ray microbeam 26 passed through pin hole P of the beam guide plate 8 also irradiates a certain scanning area of the object body 10 two-dimensionally as shown in FIG. 4. At the same time, the transmitted X-rays are detected by the X-ray detector 9. In this case, if the window of the X-ray detector 9 is wide enough (in the direction of axis 12) to receive all the X-rays transmitted through said scanning area of the object body 10, it is not necessary to shift the X-ray detector 9. However, if the window of the detector 9 is not wide enough, it becomes necessary to use a shifting means (not shown) to shift said detector 9 in the direction of the axis 12, for example, from position 9a to position 9b (see FIG. 4), depending on the value of the scanning signal generator 21 output signal. The shifting means is attached to the rotatable supporting member 11. The output signal of the detector 9 is applied to the image display means 17 via amplifier 16 and switching circuit 18. Moreover, since the scanning signal from the scanning signal generator 21 is also applied to the image display means 17 via switching circuit 18, said image display means is synchronized with the X-ray microbeam scan. Consequently, an X-ray projection image is displayed on the image display means 17. This display image may be used for determining the position of the cross-sectional slice plane 23 intended for observation.

Figure 5:
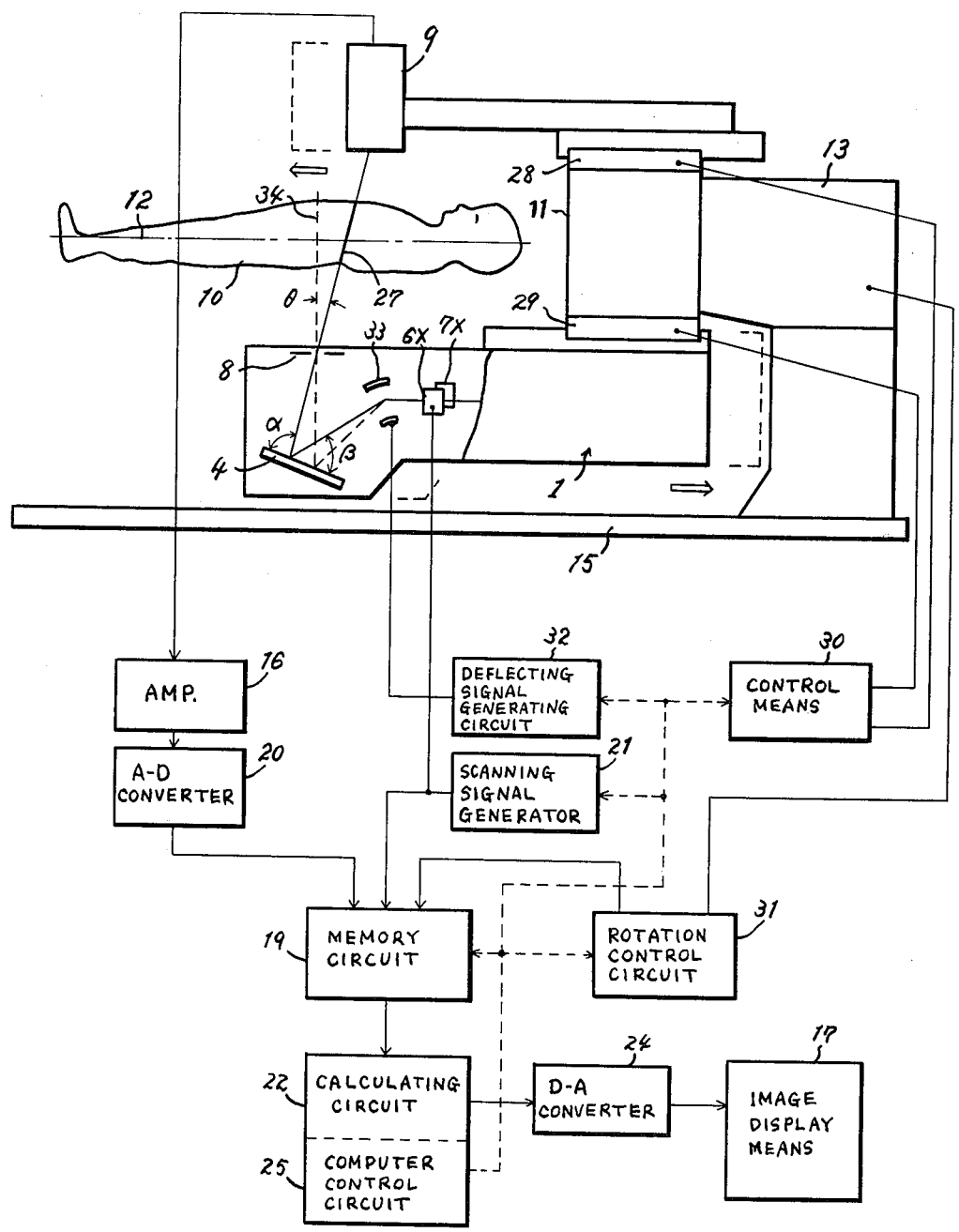
FIG. 5 is schematic drawing showing another embodiment of this invention.

FIG. 5 shows another embodiment of this invention capable of producing an X-ray image of a cross-sectional slice plane 27 inclined with respect to the cross-sectional slice plane 23. Note that plane 23 was perpendicular to the axis 12 of the object 10. The apparatus of FIG. 5 includes shifting means 28 and 29 which serve to shift the X-ray detector 9 and vacuum column 1 in parallel with the axis 12 by controlling said shifting means 28 and 29 through a control means 30 which is in turn controlled by the output signal from the computer control circuit 25. The movements of the above shifting means satisfy the relationship shown in FIG. 6 corresponding to the movement of driving means 13 which is also controlled by computer control circuit 25 via a rotation control circuit 31. In FIG. 6, the horizontal axis indicates the amount of shift z in the direction of the axis 12 and the vertical axis indicates the rotating angle $\phi$ about the axis 12. The solid line $a'$ corresponds to the position of the pin hole P and the broken line $b'$ corresponds to the position of the X-ray detector 9. The computer control circuit 25 also controls the scanning signal generator 21 and a deflection signal generating circuit 32 connected to a deflecting means 33 which is used for varying the angle $\theta$ formed by the X-ray microbeam 26 and the line 34 perpendicular to the beam guide plate 8. Namely, the computer control circuit 25 controls angle $\theta$ and the position of pin hole P so that the X-ray microbeam 26 always irradiates the inclined cross-sectional slice plane 27 regardless of the rotating angle $\phi$.

When the computer control circuit 25 applies control signals (dashed lines on FIG. 5) to the various circuits in order to irradiate the inclined cross-sectional plane as mentioned above, the transmitted X-rays are detected by the X-ray detector 9 and memorized by the memory circuit 19 via the A-D converter 20 together with the output signals from the scanning signal generator 21 and the rotation control circuit 31. The memorized data is then read out by the calculating circuit 22 and the X-ray absorption coefficient of each matrix area on the inclined cross-sectional slice plane 27 is obtained therefrom. After which, the calculated results from the calculating circuit 22 are fed into the image display means 17 via D-A converter 24 in order to display an X-ray image of the inclined cross-sectional slice plane of the object.

Incidentally, even if angle $\theta$ is zero, the electron beam is deflected by the deflecting means 33 away from the axis 12 as shown in FIG. 5. The reason for this is to increase the X-ray microbeam intensity by increasing the take-off angle $\alpha$ of the X-ray microbeam from the target 4 and the incident angle $\beta$ of the electron beam. As mentioned above, it is possible to dispense with the shifting means 28 by utilizing an X-ray detector having a large window. Moreover, if the X-ray detector is equipped with an annular window, it is not necessary to rotate the X-ray detector 9.

FIG. 7 shows the beam guide plate 8 of the embodiments according to FIGS. 1 and 5 in detail. In the figure, a thin film filter 35 made of aluminum, copper, or any other element with a certain atomic number, is arranged in the pin hole P of the beam guide plate 8. By so doing, the low energy of the white X-ray component, which forms part of the X-rays 36a and 36b, is reduced. The reduction effect of the filter is more constant than would be the case if the filter is arranged at 35b. This is because at 35b, the X-ray microbeam would pass through the filter with a greater spread and the X-rays would therefore be subjected to inconsistencies due to the slight variations in the thickness of the filter caused by processing imperfections.

An X-ray image on the inclined slice plane can be obtained without inclining the X-ray microbean. FIG. 8 is a drawing showing one method for obtaining the above X-ray image on the inclined slice plane. In the figure, 37a, 37b, . . . , 37d show slice planes of the object 10, said slice planes, which are perpendicular to the axis of said object 10, being irradiated by the X-ray microbeam in consecutive order. This is carried out with the apparatus shown in FIG. 5 by using the shifting means 28 and 29. The X-ray coefficient at each matrix area on each slice plane is calculated as explained in the embodiments shown in FIGS. 1 and 5, and is once memorized in the memory circuit 19. Moreover, the desired inclined slice plane 38 is designated by the computer control circuit 25 which reads out the calculated values relating to the cross lines 38a, 38b, . . . , 38d which cross said slice planes 37a, 37b, . . . , 37d and said supposed slice plane 38. After which, the readout values are applied to the image display means 17 via the D-A converter 24, in ordr to display an X-ray image of the desired inclined slice plane 38.

If an organism, for example particularly a human body, pulmonary, renal, vascular, cerebral, etc., is measured as an object by means of the above embodiment, the X-ray image of the sectional slice plane will be partially blurred because, at present, the measuring time is longer than the variation periods of the various organs constituting the body. In order to compensate for this, the embodiment shown in FIG. 9 incorporates a monitor 39 which serves to detect said variation periods as electric signals by monitoring the electric currents, sounds or movements generated by a specific part of the body. The output signals of the monitor 39 are memorized by the memory circuit 19 together with the output signals of the scanning signal generator 21, rotation control means 31 an X-ray detector 9. From the memorized data, only information appertaining to a specific condition of the selected organ is supplied to the calculating circuit 22 by the computer control circuit 25. By so doing, the image display means 17 is able to display still X-ray images of the cross-sectional slice plane at any one of the various conditions of the body by designating the read-out condition in the computer control circuit 25.

Figure 9:
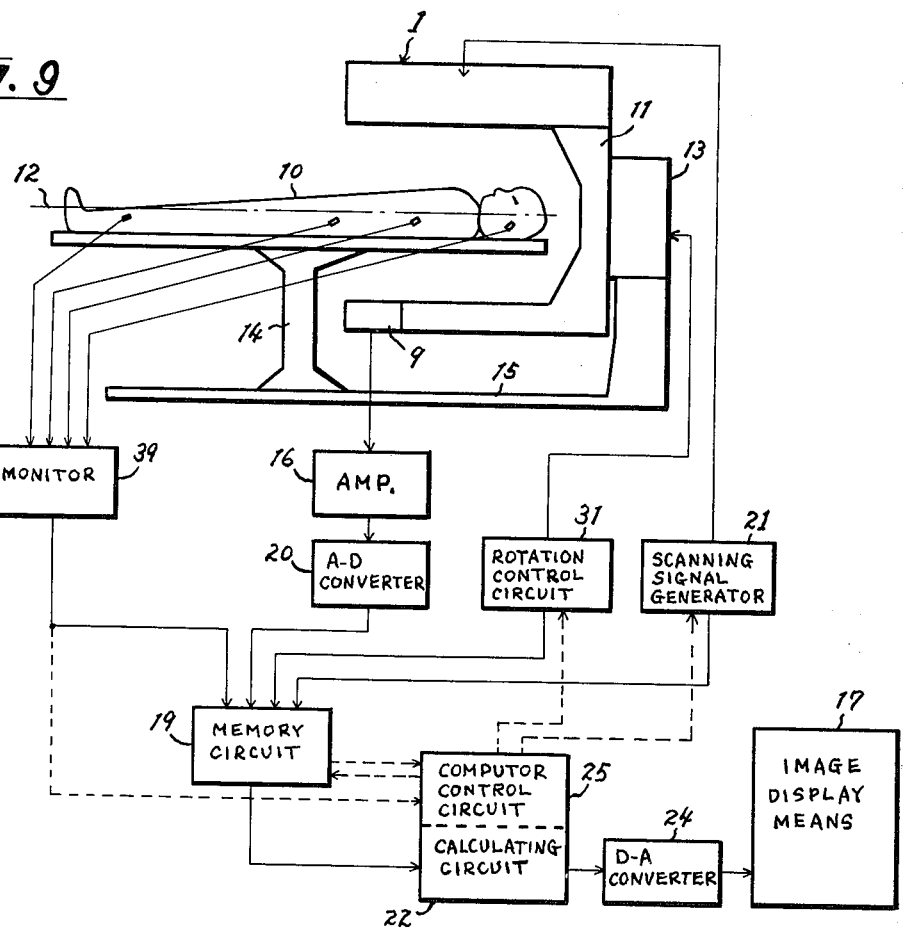
FIGS. 9 and 10 are block schematic drawings showing further embodiments of this invention.

Further, if an X-ray image on the slice plane at only one specific condition is required, it is desirable to supply the output signal of the monitor 39 directly to the computer control circuit 25 as shown by the broken line in FIG. 9. By so doing, the computer control circuit 25 operates the X-ray generating apparatus and its shifting means according to the result of analysis of the monitoring signals, thereby subjecting the body to only the amount of X-ray irradiation necessary for actual measurement.

Figure 10:
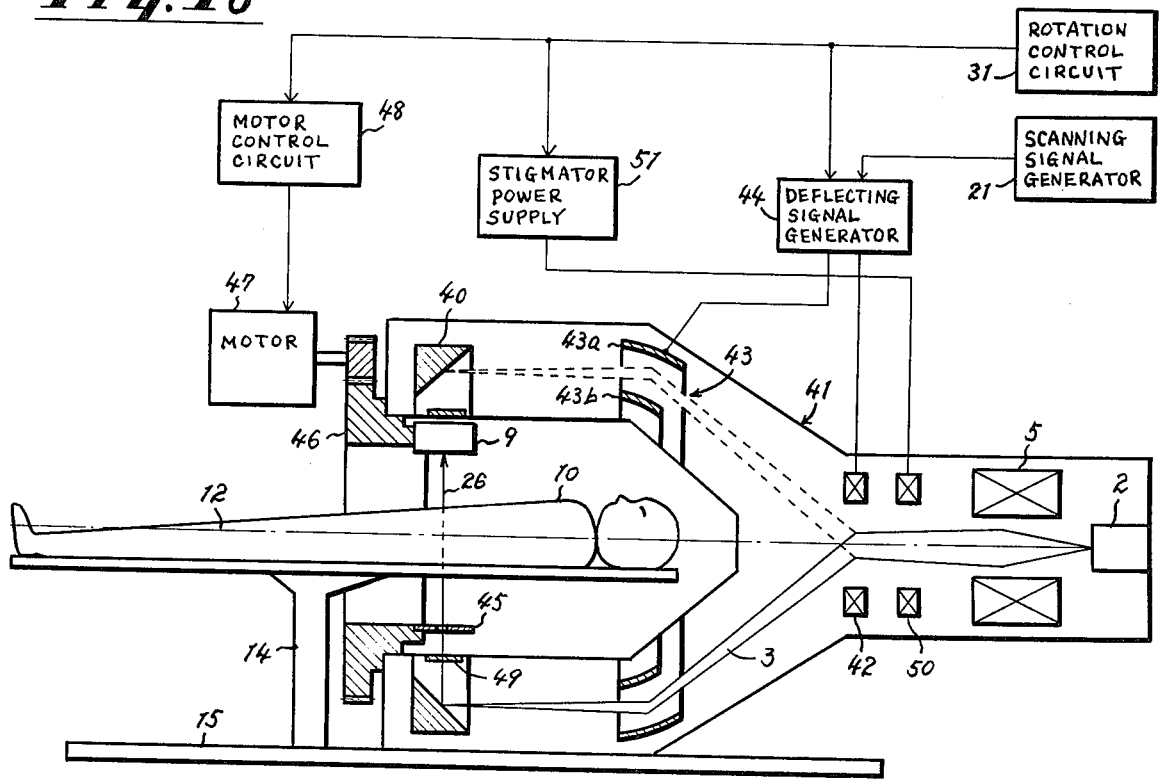

FIG. 10 shows the embodiment according to this invention which incorporates an annular target 40 located at one end of funnel-shaped vacuum column 41. The electron beam 3 generated by the electron beam source 2 is focused by the condenser lens 5 and deflected by deflecting means 42 and 43, so that a fine diameter beam irradiates the surface of the annular target 40. The deflecting means 42 and 43 are supplied with signals from the deflecting signal generator 44 so as to change the beam irradiating position continuously or digitally along the periphery of the target. The deflecting signal generator 44 is in turn controlled by the output signals of the scanning signal generator 21 and the rotating control circuit 31. The beam guide plate 45 is attached to an annular supporting member 46 which in turn is rotated about its center axis coaxially with the axis 12 of the body 10. The position of the beam guide plate 45 is changed circumferentially by means of a motor 47 which rotates the annular supporting member 46. The rotation of the electron beam 3 is controlled as motor 47 is controlled by the rotation control circuit 31 via a motor control circuit 48. By so doing, the X-ray microbeam 26, which passes through an annular filter 49 and the pin hole of the beam guide plate 45, heads toward the center axis 12 at right angles and is then detected by the X-ray detector 9 attached to the supporting member 46. Accordingly, the deflecting signal generator 44 and the deflecting means 42 and 43 respectively work as the driving means 13 and the scanning means 6X and 7X shown in FIG. 1. Moreover, in this embodiment, the measuring time for obtaiing one X-ray image is shorter than that of the aforementioned embodiments, since the driving means 13 for rotating X-ray generating column 1 is not incorporated. A stigmator 50 and stigmator power supply 51 are controlled by the rotation control circuit 31. The stigmator 50 is used to compensate for distortion of the cross-sectional shape of the electron beam at the target surface caused by the deflecting means 42 and 43.

It is possible to irradiate the annular target 40 by using only a single stage deflecting means and its power supply. However, it is better to incorporate a two or more stage deflecting means, as in the case of the embodiment, shown in FIG. 10, as this allows the funnel-shaped portion of the apparatus to be made more commodious for the reclining object body without enlarging the apparatus as a whole. Further, in the two or more stage deflecting means, it is preferable to use an electrostatic deflecting means for the second or successive stages rather than a magnetic deflecting means as a large current power supply is needed in the case of the magnetic deflecting means in the second and subsequent stages, whereas in the case of the electrostatic deflecting means comprising two ring-shaped coaxial deflecting plates 43a and 43b as shown in FIG. 10, the electron beam can be deflected by a comparatively small voltage power supply.

Figure 11:
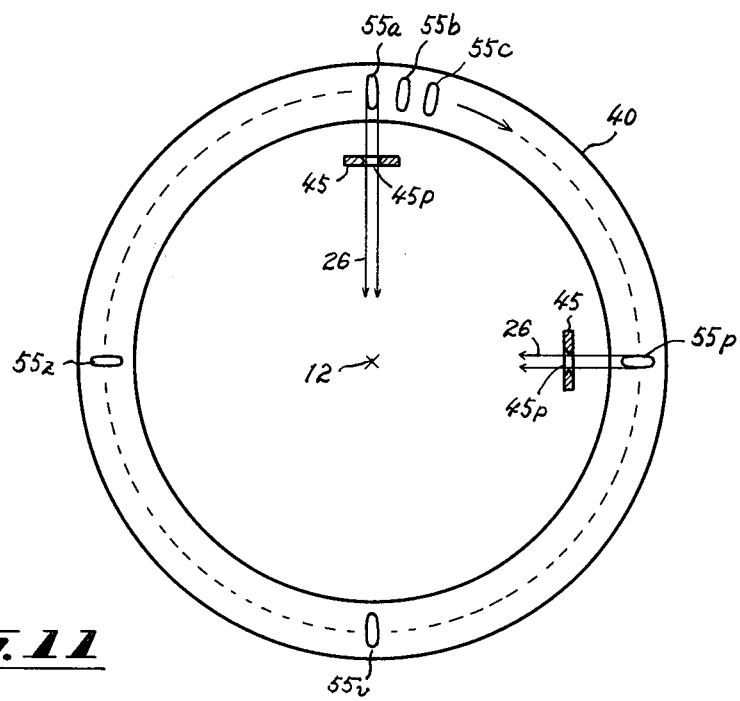
FIG. 11 is a drawing for explaining the embodiment shown in FIG. 10.

Additionally, with an electrostatic deflecting means, the cross-sectional shape of the electron beam at the target surface can be changed at will as shown in FIG. 11. To be more explicit, since the cross-sectional shapes 55a, 55b, and 55c on the target 40 are elliptical and their longitudinal axes are always orientated radially with respect to the axis 12, a strong intensity X-ray microbeam having a circular cross-sectional and a comparatively low electron beam intensity per target unit area is taken off through the pin hole 45p. The stigmator 50 and its power supply 51 in FIG. 10 provide the means for changing the cross-sectional shape of the electron beam.

Figure 12:
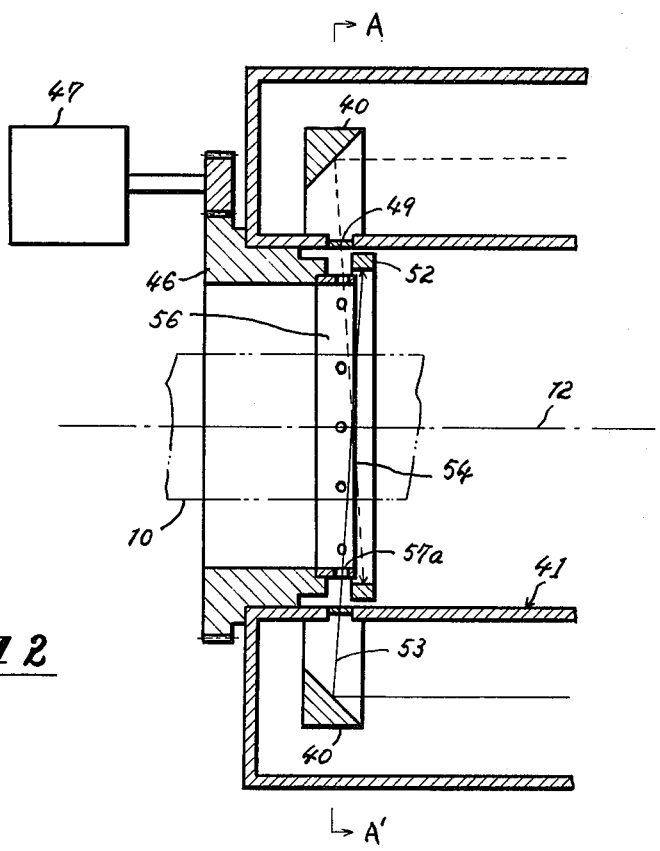
FIG. 12 shows the essential part of yet another embodiment according to this invention.

FIG. 12 shows the essential part of a modified embodiment of FIG. 10. In this embodiment in which a fixed annular detector 52 is incorporated, the radiant direction of the X-ray 53 for irradiating the object body 10 is slightly inclined with respect to the plane 54. A detector 52 suitably located so that the X-ray passed through the object body 10 is detected without being intercepted.

Figure 13:
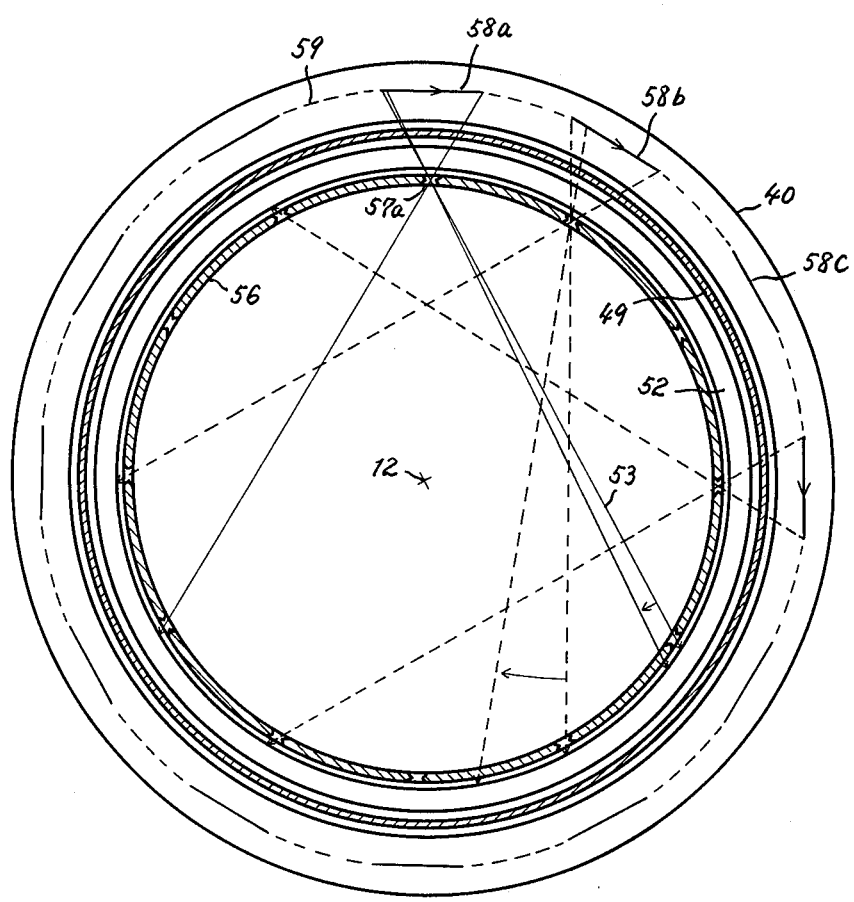
FIG. 13 is a drawing for explaining the embodiment shown in FIG. 12.

In this embodiment, if the rotating member 46 is rotated at the same angular speed as the angular deflection speed of the electron beam 3, the X-ray microbeam will pass through only one of the pin holes of the beam guide plate 56. Even if the rotating member 46 is held fixed, the X-ray microbeam is still able to irradiate the object body at various angles. In this case, the measuring time is much shorter than in the case of the previously described embodiments, since in this embodiment, no mechanical rotating means are used. The relation between the electron beam deflection pattern on the target and the pin holes 55a, 55b, . . . etc. is schematically shown in FIG. 13 which represents a cross-sectional view of FIG. 12 through AA'. In FIG. 13, the solid lines 58a, 58b, . . . , etc. superimposing the hatched circle 59 represent the electron beam irradiating lines (micro areas). Accordingly, the X-ray microbeam scans the object body 10 at each pin hole; viz.; 57a, 57b, . . . , etc. However, if for one reason or another, it is impossible to increase the number of pin holes sufficiently, the X-ray data for forming an X-ray image of a cross-sectional plane of the object body will be insufficient. That is unless, for example, the beam guide plate is rotated at a speed lower than and in synchronism with that of the electron beam deflection. By so doing, while the actual number of pin holes remains the same, the effective number increases. Accordingly, adequate data for forming the above X-ray image can be obtained.

Additionally, it is possible to use a partially annular target, filter and detector instead of the fully annular target 40, filter 49 and detectors 9 and 52.

Having thus described my invention with the detail and particularity as required by the patent laws, what is desired protected by Letters Patent is set forth in the following claims.

What is claimed is:

1. An apparatus for obtaining a two dimensional display of the X-ray absorption distribution on a cross-sectional plane of an object comprising:
   a. means for generating an electron beam, b. means for focusing said electron beam on a target thereby generating X-radiation at the location of impingement, c. a guide plate having a pin hole therein for forming and directing an X-ray microbeam onto the object, d. means for scanning said electron beam over the surface of the target to cause the X-ray microbeam to correspondingly scan a cross-sectional plane of the object, e. means for rotating said generating means, focusing means, guide plate and scanning means around the object, f. means for detecting and measuring the intensity of the X-rays passed through the object, g. a memory for memorizing the output of said detecting means along with the corresponding output signals from the scanning means and the rotating means, h. means for calculating the absorption value at each micro matric area on said cross-sectional plane from the data memorized in the memory, and i. means for displaying said respective calculated absorption values two-dimensionally.

2. An apparatus according to claim 1 for alternately providing a X-ray projecton image of the object wherein said scanning means comprises means for scanning the electron beam two-dimensionally over the surface of the target, the display means comprises means for providing a raster synchronized with the scanning means, and means for applying the output of said detecting means as a brightness modulation signal to the display means.

3. An apparatus according to claim 1 including means for shifting said generating means, focusing means, and guide plate parallel with the rotating axis of the rotating means so that the X-ray microbeam may scan a cross-sectional plane not perpendicular to the rotating axis.

4. An apparatus according to claim 1, wherein the electron beam generated by the electron beam source is deflected away from the rotating axis of said rotating means so as to increase the take-off angle of the X-ray microbeam.

5. An apparatus as claimed in claim 1, wherein a film filter is centrally arranged in the guide plate pin hole.

6. An apparatus according to claim 1 comprising a signal generator which controls the scanning means in response to a signal indicative of a change in the object.

7. An apparatus according to claim 1, wherein the calculating means incorporates a means for sampling the data memorized in the memory according to the output of a signal generator which monitors changes in the object.

8. An apparatus for obtaining a two-dimensional display of the X-ray absorption distribution on a cross-sectional plane of an object comprising:

a. means for generating an electron beam directed along a center beam axis, b. an annulr or partially annular target having a conical surface, the axis of which coincides with the axis of the center beam generated by the electron beam source, c. a means for deflecting said electron beam from the center beam axis to the target, d. a means for rotating said electron beam around the target thereby generating X-radiation at the location of impingement, e. a beam guide having a pin hole or pin holes for directing the X-ray microbeam onto the object, f. a detecting means for detecting and measuring the intensity of the X-ray passed through the object, g. a memory for memorizing the output of said detecting means along with the corresponding output signals from the rotating means, h. means for calculating the absorption value at each micro matric area on said cross-sectional plane from the data memorized in the memory, and i. means for displaying said respective calculated absorption values two dimensionally.

9. An apparatus according to claim 8, wherein said rotating means incorporates plural deflecting stages.

10. An apparatus according to claim 9, wherein one of said plural deflecting stage comprises an electrostatic deflecting plate.

11. An apparatus according to claim 8, wherein said beam guide is rotated by a mechanical rotating means in synchronism with said rotating means.

12. An apparatus according to claim 8, wherein said beam guide is fixed.

13. An apparatus according to claim 8, wherein the shape of said detecting means is annular or partially annular and is fixed.

14. An apparatus for obtaining a two-dimensional display of the X-ray absorption distribution on a cross-sectional plane of an object comprising:

a. means for generating an electron beam directed along a center beam axis, b. an annular or partially annular target having a conical surface, the center axis of which coincides with the axis of the center beam generated by the electron beam source, c. means for deflecting said electron beam from said center beam to the target, d. a means for rotating the electron beam around the target thereby generating X-radiation at the location of impingement, e. a stigmator for changing the cross-sectional shape of the electron beam in synchronism with the rotating means, f. a beam guide having a pin hole or pin holes for directing the X-ray microbeam upon the object, g. a detecting means for detecting and measuring the intensity of the X-ray passed through the object, h. a memory for memorizing the output of said detecting means along with the corresponding output signals from the rotating means, i. a calculating means for calculating the absorption value at each micro matrix area on said cross-sectional plane from the data memorized in the memory, and j. a display means for displaying said respective calculated absorption values two-dimensionally.

* * * * *